(12) United States Patent
Yin et al.

(10) Patent No.: US 11,976,091 B2
(45) Date of Patent: May 7, 2024

(54) TERPENE GLYCOSIDE DERIVATIVES AND USES THEREOF

(71) Applicant: Firmenich SA, Satigny (CH)

(72) Inventors: Dan-Ting Yin, Shanghai (CN); Yi-Min Wang, Shanghai (CN); Xian-Wen Gan, Shanghai (CN)

(73) Assignee: Firmenich SA, Satigny (CH)

( * ) Notice: Subject to any disclaimer, the term of this patent is extended or adjusted under 35 U.S.C. 154(b) by 429 days.

(21) Appl. No.: 17/252,269

(22) PCT Filed: Sep. 25, 2019

(86) PCT No.: PCT/EP2019/075784
§ 371 (c)(1),
(2) Date: Dec. 15, 2020

(87) PCT Pub. No.: WO2020/064788
PCT Pub. Date: Apr. 2, 2020

(65) Prior Publication Data
US 2021/0261593 A1    Aug. 26, 2021

(30) Foreign Application Priority Data

Sep. 29, 2018  (WO) ................ PCT/CN2018/108654

(51) Int. Cl.
*C07H 15/256*  (2006.01)
*A23L 27/30*  (2016.01)
(52) U.S. Cl.
CPC ............ *C07H 15/256* (2013.01); *A23L 27/36* (2016.08); *A23V 2002/00* (2013.01)

(58) Field of Classification Search
CPC .... C07H 15/256; A23L 27/36; A23V 2002/00
USPC .......................................................... 426/658
See application file for complete search history.

(56) References Cited

U.S. PATENT DOCUMENTS

2015/0315623 A1* 11/2015 Mao ................ C12P 19/56
  435/78
2016/0192685 A1   7/2016 Markosyan et al.
2019/0343159 A1  11/2019 Carlson et al.
2020/0377541 A1  12/2020 Pukrayastha et al.

FOREIGN PATENT DOCUMENTS

WO   2014/150127   9/2014

OTHER PUBLICATIONS

Karthaus, O. et al. J. Chem. Soc. Perkin. Trans. 1:1851 (Year: 1994).*
Dumitru, M. et al. Sci. Bull. Series F. Biotechnologies, vol. XXI (Year: 2017).*
Rao et al., Food Chem., vol. 200, pp. 154-158 (2016).
International Search Report and Written Opinion for corresponding International Application No. PCT/EP2019/075784 dated Dec. 5, 2019 (14 pages).

* cited by examiner

*Primary Examiner* — Hamid R Badr
(74) *Attorney, Agent, or Firm* — Robert S. Dailey

(57) ABSTRACT

The present disclosure relates generally to terpene glycosides, such as certain such compounds extracted from *Stevia rebaudiana* Bertoni, *Rubus* suavissimus, or Siraitia grosvenorii. The disclosure also provides for the use of such compounds as food ingredients, flavors, and sweeteners, and related methods. The disclosure also provides ingestible compositions comprising such compounds, as well as processes for extracting such compounds selectively from certain plant sources.

2 Claims, 7 Drawing Sheets

US 11,976,091 B2

TERPENE GLYCOSIDE DERIVATIVES AND USES THEREOF

CROSS-REFERENCE TO RELATED APPLICATIONS

The present application is the United States national stage patent application of PCT Application No. PCT/EP2019/075784, filed Sep. 25, 2019, which claims the benefit of priority of PCT Application No. PCT/CN2018/108654, filed Sep. 29, 2018, which is hereby incorporated by reference as though set forth herein in its entirety.

TECHNICAL FIELD

The present disclosure relates generally to terpene glycosides, such as certain such compounds extracted from *Stevia rebaudiana* Bertoni, *Rubus* suavissimus, or Siraitia grosvenorii. The disclosure also provides for the use of such compounds as food ingredients, flavors, and sweeteners, and related methods. The disclosure also provides ingestible compositions comprising such compounds, as well as processes for extracting such compounds selectively from certain plant sources.

DESCRIPTION OF RELATED ART

The taste system provides sensory information about the chemical composition of the external world. Taste transduction is one of the more sophisticated forms of chemically triggered sensation in animals. Signaling of taste is found throughout the animal kingdom, from simple metazoans to the most complex of vertebrates. Mammals are believed to have five basic taste modalities: sweet, bitter, sour, salty, and umami.

Sweetness is the taste most commonly perceived when eating foods rich in sugars. Mammals generally perceive sweetness to be a pleasurable sensation, except in excess. Caloric sweeteners, such as sucrose and fructose, are the prototypical examples of sweet substances. Although a variety of no-calorie and low-calorie substitutes exist, these caloric sweeteners are still the predominant means by which comestible products induce the perception of sweetness upon consumption.

Metabolic disorders and related conditions, such as obesity, diabetes, and cardiovascular disease, are major public health concerns throughout the world. And their prevalence is increasing at alarming rates in almost every developed country. Caloric sweeteners are a key contributor to this trend, as they are included in various packaged food and beverage products to make them more palatable to consumers. In many cases, no-calorie or low-calorie substitutes can be used in foods and beverages in place of sucrose or fructose. Even so, these compounds impart sweetness differently from caloric sweeteners, and a number of consumers fail to view them as suitable alternatives. Moreover, such compounds may be difficult to incorporate into certain products. In some instances, they may be used as partial replacements for caloric sweeteners, but their mere presence can cause many consumers to perceive an unpleasant astringency. Therefore, lower-calorie sweeteners still face certain challenges to their adoption.

Terpene glycosides, such as steviol glycosides from *Stevia* (*Stevia rebaudiana* Bertoni) extracts, rubusoside from blackberry leaf (*Rubus* suavissimus) extracts, and mogrosides from monk fruit (Siraitis grosvenorii) extracts, are natural low-calorie sweeteners. But these products, like many other low-calorie sugar alternatives, have negative taste attributes, such as bitterness, lingering aftertaste, or licorice flavor. Transglucosylation provides a way of mitigating some of these negative taste attributes. But many of the presently disclosed glucosylated low-calorie sweeteners continue to exhibit negative taste attributes that prevent their widespread adoption. Thus, there is a continuing need to develop glucosylated products and transglucosylation methods that can provide more effective mitigation of negative taste attributes.

SUMMARY

In a first aspect, the disclosure provides methods of making a glucosylated terpene glycoside, the method comprising: (a) providing an aqueous composition comprising a β-glucosyl sugar compound, a terpene glycoside, and a cellulase enzyme; and (b) reacting the β-glucosyl sugar compound with the terpene glycoside in the presence of the cellulase enzyme to form a glucosylated terpene glycoside having a terpene glycosidyl moiety and one or more β-glucosyl sugar moieties, wherein the glucosylated terpene glycoside has one β-1,6 glucosidic bond between the terpene glycoside moiety and one of the one or more β-glucosyl sugar moieties. In some embodiments, the reacting comprises incubating the aqueous composition. In some embodiments, the aqueous composition is an aqueous solution.

In a second aspect, the disclosure provides methods of reducing an unpleasant taste of a terpene glycoside, the method comprising: (a) providing an aqueous composition comprising an β-glucosyl sugar compound, a terpene glycoside, and a cellulase enzyme; and (b) reacting the β-glucosyl sugar compound with the terpene glycoside in the presence of the cellulase enzyme to form a glucosylated terpene glycoside having a terpene glycosidyl moiety and one or more β-glucosyl sugar moieties, wherein the glucosylated terpene glycoside has one β-1,6 glucosidic bond between the terpene glycoside moiety and one of the one or more β-glucosyl sugar moieties. In some embodiments, the reacting comprises incubating the aqueous composition. In some embodiments, the aqueous composition is an aqueous solution. In some embodiments, the method reduces an unpleasant licorice taste of the terpene glycoside.

In some embodiments of the foregoing aspects, the terpene glycoside is selected from the group consisting of: stevioside, rebaudioside A, rebaudioside B, rebaudioside C, rebaudioside D, rebaudioside E, rebaudioside F, rebaudioside G, rebaudioside M, dulcoside A, steviolbioside, rubusoside, terpene glycosides found in *Stevia rebaudiana* Bertoni plants, terpene glycosides found in *Rubus* suavissimus plants, terpene glycosides found in Siraitis grosvenorii plants, and mixtures thereof. In some such embodiments, the terpene glycoside is rebaudioside A.

In some embodiments of the foregoing aspects, the beta-glucosyl sugar compound is cellobiose.

In a third aspect, the disclosure provides a compound of formula I:

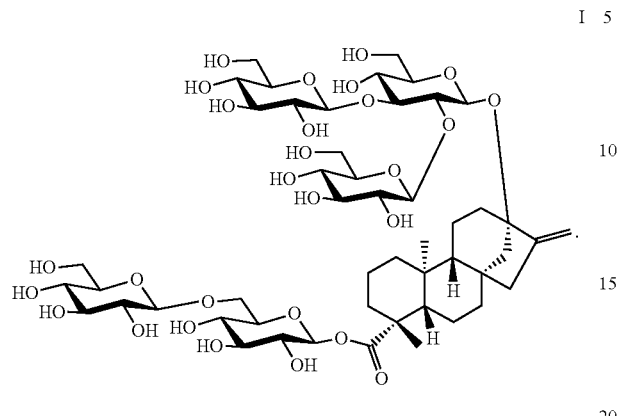

In a fourth aspect, the disclosure provides a compound of formula II:

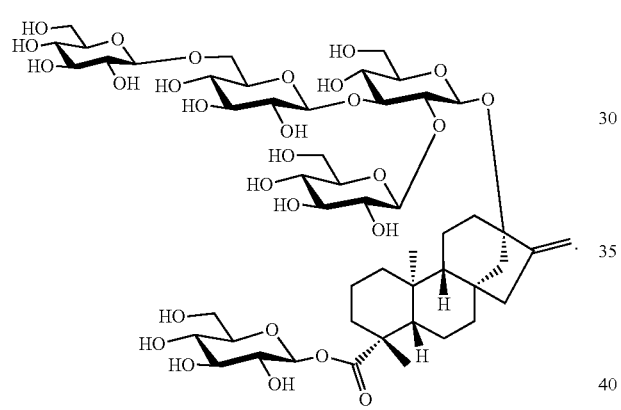

In a fifth aspect, the disclosure provides a compound of formula III:

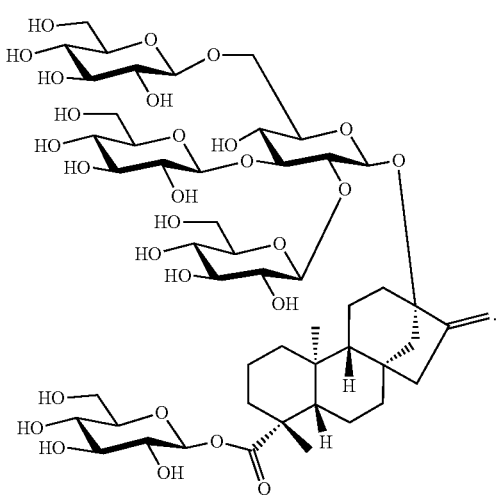

In a sixth aspect, the disclosure provides a compound of formula IV:

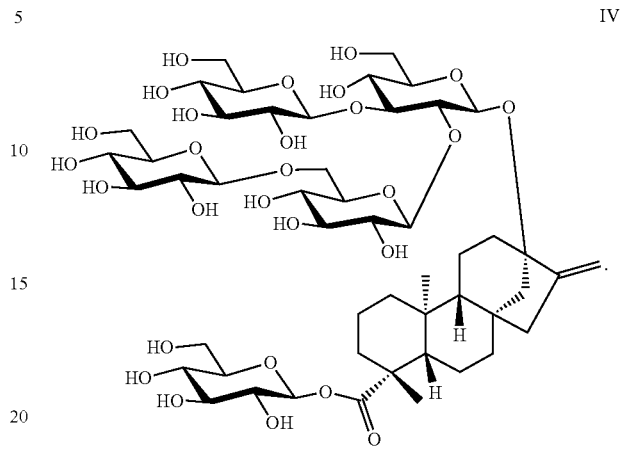

In a seventh aspect, the disclosure provides a composition comprising at least one glucosylated terpene glycoside made according to the processes of the first or second aspects. In some embodiments thereof, the glucosylated terpene glycoside is a compound of the third aspect, or a compound of the fourth aspect, or a compound of the fifth aspect, or a compound of the sixth aspect. In some further embodiments of any of the foregoing embodiments, the glucosylated terpene glycosides in the composition confer, enhance, improve, or modify a sweet taste of a flavored article. In some such embodiments, the terpene glycosides are present in the composition in an amount effective to confer, enhance, improve, or modify the sweet taste of the composition. In some embodiments, the composition is a flavored article. In some embodiments, the composition is not a naturally occurring composition.

In an eighth aspect, the disclosure provides uses of any of the compounds of the third through the sixth aspects, or any compositions of the seventh aspect to modify the flavor of a composition, such as an ingestible composition. In some further embodiments, the use comprises enhancing the sweetness of an ingestible composition. In some other embodiments, the use comprises reducing the bitterness or reducing a lingering licorice taste of an ingestible composition. In some embodiments thereof, the composition comprises a sweetener, such as a non-caloric or caloric sweetener.

BRIEF DESCRIPTION OF THE DRAWINGS

The following drawings are provided for purposes of illustrating various embodiments of the compositions and methods disclosed herein. The drawings are provided for illustrative purposes only, and are not intended to describe any preferred compositions or preferred methods, or to serve as a source of any limitations on the scope of the claimed inventions.

DETAILED DESCRIPTION

Figure 1:
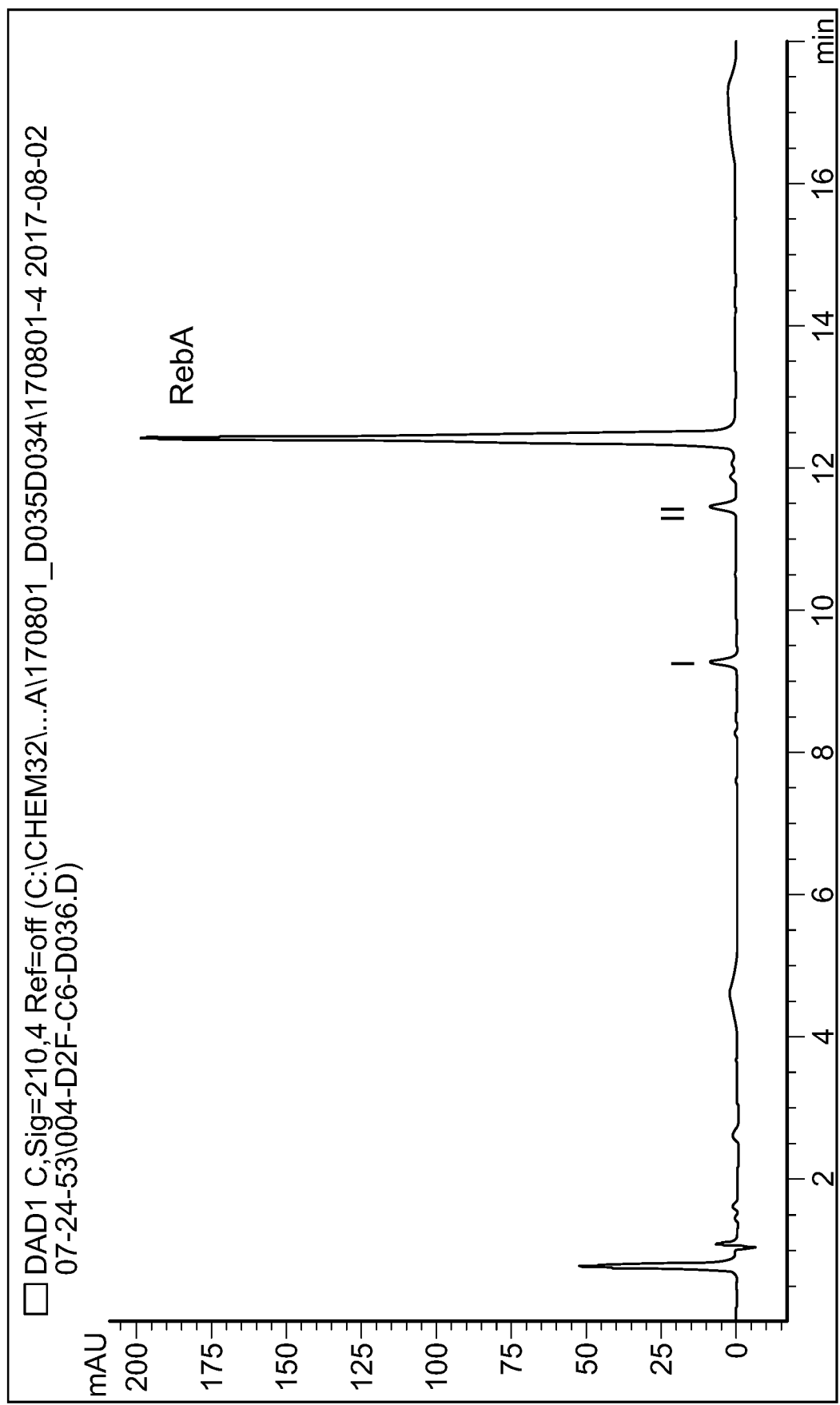
FIG. 1 shows an HPLC chromatogram of the product enzymatically generated by cellulase with rebaudioside A and cellobiose as substrates.

In the following description, reference is made to specific embodiments which may be practiced, which is shown by way of illustration. These embodiments are described in detail to enable those skilled in the art to practice the invention described herein, and it is to be understood that other embodiments may be utilized and that logical changes may be made without departing from the scope of the aspects presented herein. The following description of example embodiments is, therefore, not to be taken in a limited sense, and the scope of the various aspects presented herein is defined by the appended claims.

Methods

In a certain aspects, the disclosure provides methods of making a glucosylated terpene glycoside, the method comprising: (a) providing an aqueous composition comprising a β-glucosyl sugar compound, a terpene glycoside, and a cellulase enzyme; and (b) reacting the β-glucosyl sugar compound with the terpene glycoside in the presence of the cellulase enzyme to form a glucosylated terpene glycoside having a terpene glycosidyl moiety and one or more β-glucosyl sugar moieties, wherein the glucosylated terpene glycoside has one β-1,6 glucosidic bond between the terpene glycoside moiety and one of the one or more β-glucosyl sugar moieties. In some embodiments, the reacting comprises incubating the aqueous composition. In some embodiments, the aqueous composition is an aqueous solution.

In certain related aspects, the disclosure provides methods of reducing an unpleasant taste of a terpene glycoside, the method comprising: (a) providing an aqueous composition comprising an β-glucosyl sugar compound, a terpene glycoside, and a cellulase enzyme; and (b) reacting the β-glucosyl sugar compound with the terpene glycoside in the presence of the cellulase enzyme to form a glucosylated terpene glycoside having a terpene glycosidyl moiety and one or more β-glucosyl sugar moieties, wherein the glucosylated terpene glycoside has one β-1,6 glucosidic bond between the terpene glycoside moiety and one of the one or more β-glucosyl sugar moieties. In some embodiments, the reacting comprises incubating the aqueous composition. In some embodiments, the aqueous composition is an aqueous solution. In some embodiments, the method reduces an unpleasant licorice taste of the terpene glycoside.

In some embodiments, the disclosure provides enzymatic processes for producing glucosylated forms of stevioside, rebaudioside A, rebaudioside B, rebaudioside C, rebaudioside D, rebaudioside E, rebaudioside F, rebaudioside G, rebaudioside M, dulcoside A, steviolbioside, rubusoside, terpene glycosides found in *Stevia rebaudiana* Bertoni plants, terpene glycosides found in *Rubus* suavissimus plants, terpene glycosides found in Siraitis grosvenorii plants, or mixtures thereof.

In some embodiments, the starting material for the enzymatic process is an extract of a *Stevia rebaudiana* Bertoni plant, or, alternatively, an extract of a *Rubus* suavissimus plants, or, alternatively, an extract of a Siraitis grosvenorii plant. In some embodiments, the plant extracts contain one, or more than one terpene glycoside.

For example, by way of illustration, *Stevia rebaudiana* Bertoni, produces a number of diterpene glycosides, including stevioside, rebaudioside A, rebaudioside B, rebaudioside C, rebaudioside D, rebaudioside E, rebaudioside F, rebaudioside G, rebaudioside M, dulcoside A, and steviolbioside. As another example, rubusoside may be obtained from, but not limited to blackberry leaves (*Rubus* suavissimus), containing substantially a single terpene glycoside called rubusoside. Rubusoside may also be found in low amounts in *stevia* leaves. Rubusoside may also be found in extracts of *stevia* leaves (*Stevia rebaudiana* Bertoni).

In some other embodiments, the starting material for the enzymatic process may be a terpene glycoside purified from either an extract of a *Stevia rebaudiana* Bertoni plants, or an extract of a *Rubus* suavissimus plants, or an extract of a Siraitis grosvenorii plant.

In some embodiments, the terpene glycoside starting material is selected from the group consisting of: stevioside, rebaudioside A, rebaudioside B, rebaudioside C, rebaudioside D, rebaudioside E, rebaudioside F, rebaudioside G, rebaudioside M, dulcoside A, steviolbioside, rubusoside, and mixtures thereof.

In some embodiments, the terpene glycoside starting material is selected from the group consisting of: stevioside, rebaudioside A, rebaudioside B, rebaudioside C, and rubusoside. In some embodiments, the terpene glycoside starting material is rebaudioside A.

In some embodiments, the terpene glycoside starting material is the starting material disclosed in U.S. Pat. No. 8,257,948.

In some embodiments, the terpene glycoside starting material is the starting material disclosed in PCT Publication No. WO 2017/089444.

In some embodiments, the terpene glycoside starting material is the starting material disclosed in PCT Publication No. WO 2013/019050.

In some embodiments, the terpene glycoside starting material is the starting material disclosed in European Patent Application Publication No. 3003058.

In some embodiments of the methods disclosed herein, the method includes the step of forming an aqueous composition (e.g., an aqueous solution) comprising a mixture of an beta-glucosyl sugar compound, a terpene glycoside and a cellulase. In some further such embodiments, the method further includes the step of incubating the aqueous composition to generate the glucosylated terpene glycoside having a single glucosyl residue linked to the terpene glycoside via a β-1,6 glucosidic bond.

As used herein, the term "glycoside" refers to an organic compound to which one or more sugar units are covalently bound at one or more sites of the chemical structure.

In some embodiments, the aqueous composition is an aqueous solution. In some such embodiments, the carrier is deionized water. Alternatively, in some embodiments, the aqueous composition comprises sodium acetate.

The aqueous composition can have any suitable pH value. In some embodiments, the pH of the aqueous composition ranges from pH 4.0 to pH 7.0. In some embodiments, the pH of the aqueous composition ranges from pH 4.0 to pH 6.0. In some embodiments, the pH of the aqueous solution ranges from pH 4.0 to pH 5.0. In some embodiments, the pH of the aqueous composition ranges from pH 5.0 to pH 7.0. In some embodiments, the pH of the aqueous composition ranges from pH 6.0 to pH 7.0. In some embodiments, the pH of the aqueous composition is pH 4.0, or 4.1, or 4.2, or 4.3, or 4.4, or 4.5, or 4.6, or 4.7, or 4.8, or 4.9, or 5.0, or 5.1, or 5.2, or 5.3, or 5.4, or 5.5, or 5.6, or 5.7, or 5.8, or 5.9, or 6.0, or 6.1, or 6.2, or 6.3, or 6.4, or 6.5, or 6.6, or 6.7, or 6.8, or 6.9, or 7.0. In some embodiments, the pH of the aqueous composition is pH 5.0.

The terpene glycoside can be included in the aqueous composition in any suitable concentration. In some embodiments, the terpene glucoside is included in the aqueous composition at a concentration ranging from 0.005 g/mL to 0.5 g/mL, or from 0.02 g/mL to 0.2 g/mL, or from 0.04 g/mL to 0.12 g/mL.

Any suitable beta-glucosyl sugar compound can be used in the methods disclosed herein. In some embodiments, the beta-glucosyl sugar compound is a reducing sugar having two β-glucose molecules linked by a β-1,4 bond. In some embodiments, the beta-glucosyl sugar compound is selected from the group consisting of: cellotriose, cellotetraose, cellopentaose, and cellohexaose. In some embodiments, the beta-glucosyl sugar compound is a cellodextrin. In some embodiments, the beta-glucosyl sugar compound is a cellulose, or a derivative thereof. In some embodiments, the beta-glucosyl sugar compound is cellobiose.

The beta-glucosyl sugar compound can be included in the composition at any suitable concentration. In some embodiments, the concentration of the beta-glucosyl sugar compound in the aqueous composition ranges from 1 wt % to 40 wt %. In some embodiments, the concentration of the beta-glucosyl sugar compound in the aqueous solution ranges from 2 wt % to 30 wt %, or from 5 wt % to 20 wt %. In some embodiments, the concentration of the beta-glucosyl sugar compound in the aqueous composition ranges from 0.005 g/mL to 0.5 g/mL. In some embodiments, the concentration of the beta-glucosyl sugar compound in the aqueous composition is about 0.04 g/mL.

In the methods disclosed herein, the ratio of the terpene glycoside to the beta-glucosyl sugar compound can have any suitable value. In some embodiments, the ratio of the terpene glycoside to the beta-glucosyl sugar compound in the aqueous composition ranges from 100:1 to 1:100, or from 10:1 to 1:10. In some embodiments, the ratio of the terpene glycoside to the beta-glucosyl sugar compound in the aqueous composition is about 1:1.

In some embodiments, the cellulase performs a transglucosylation reaction, thereby generating glucosylated terpene glycoside having a single glucosyl residue linked to the terpene glycoside via a β-1,6 glucosidic bond. Alternatively, in some embodiments, the transglucosidase performs a transglucosylation reaction, thereby generating a glucosylated terpene glycoside having one or more glucose residues covalently attached to the terpene glycoside via a β-1,6 glucosidic bond. In some embodiments, the number of glucose residues that are added to the terpene glycoside may be controlled by parameters such as, for example, the time of the reaction, the temperature of the reaction, the concentration of the terpene glycoside, the concentration of the beta-glucosyl sugar compound, and the like.

In some embodiments, the cellulase may perform the transglucosylation reaction, using cellobiose as a substrate, thereby generating a glucosylated terpene glycoside wherein two glucose units are added to the terpene glycoside via a β-1,6 glucosidic bond.

The cellulase can be in any suitable form. In some embodiments, the cellulase is in a form of cell-free culture broth, concentrated liquid cell-free culture broth, spray dried or freeze dried cell-free culture broth, or high purity protein. Free and immobilized enzyme preparations may also be used.

Several different kinds of cellulases are suitable, which differ structurally and mechanistically. Synonyms, derivatives, and specific enzymes associated with the name "cellulase" include endo-1,4-beta-D-glucanase (beta-1,4-glucanase, beta-1,4-endoglucan hydrolase, endoglucanase D, 1,4-(1,3,1,4)-beta-D-glucan 4-glucanohydrolase), carboxymethyl cellulase (CMCase), avicelase, celludextrinase, cellulase A, cellulosin AP, alkali cellulase, cellulase A 3, 9.5 cellulase, beta-glucosidase, cellulose 1,4-beta-cellobiosidase and pancellase SS.

The cellulase can be included at any suitable concentration. In some embodiments, the cellulase is included in the aqueous composition at a concentration ranging from 0.2 to 0.4 units per gram of beta-glucosyl sugar compound. In some embodiments, the cellulase is included in the aqueous solution at a concentration ranging from 2 mg/mL to 200 mg/mL. In some embodiments, the cellulase is included in the aqueous composition at a concentration of about 40 mg/mL.

In some embodiments, the ratio of the amount of enzyme in wt % to the amount of terpene glycoside in wt % ranges from 0.1% to 500%, or from 10% to 200%, or from 50% to 150%.

In some embodiments, the mixture containing the cellulase is incubated for a time and temperature sufficient to generate the glucosylated terpene glycoside. In some embodiments, the glucosylated terpene glycoside is a glucosylated terpene glycoside having a single glucosyl residue linked to the terpene glycoside via a β-1,6 glucosidic bond.

Any suitable temperature can be used for the incubation. In some embodiments, the temperature ranges from 30° C. to 90° C., or from 70° C. to 90° C. In some embodiments, the temperature is about 60° C. In some embodiments, the temperature is about 37° C.

The incubation can be carried out for any suitable length of time. In some embodiments, the time is 24 hours or greater. Alternatively, in some other embodiments, the time is 24 hours or less. In some embodiments, the time is 24 hours, or 23 hours, or 22 hours, or 21 hours, or 20 hours, or 19 hours, or 18 hours, or 17 hours, or 16 hours, or 15 hours, or 14 hours, or 13 hours, or 12 hours, or 11 hours, or 10 hours, or 9 hours, or 8 hours, or 7 hours, or 6 hours, or 5 hours, or 4 hours, or 3 hours, or 2 hours, or 1 hour. In some embodiments, the time is about 24 hours.

In some embodiments, after the incubation step, the mixture containing the glucosylated terpene glycoside may treated further. Such further treatment may include, for example, an inactivation step and/or a purification step, wherein the glucosylated terpene glycoside is isolated or purified. In some embodiments, the glucosylated terpene glycoside is a glucosylated terpene glycoside having a single glucosyl residue linked to the terpene glycoside via a β-1,6 glucosidic bond.

Non-limiting examples of the purification step include enrichment, isolation and/or purification of the glucosylated terpene glycoside, or the removal of solids from the reaction mixture. In some embodiments, the glucosylated terpene glycoside is a glucosylated terpene glycoside having a single glucosyl residue linked to the terpene glycoside via a β-1,6 glucosidic bond. In some embodiments, solids are removed from the reaction mixture by means such as filtration, centrifugation, or other techniques known to those skilled in the art.

In some embodiments, carbohydrates are removed from the mixture using adsorption resins, precipitation, or other techniques known to those skilled in the art. In some embodiments, the further treatment may comprise inactivating the cellulase. In one example, the cellulase is inactivated by the application of heat. In some embodiments, the cellulase is inactivated by heating the reaction mixture to a temperature sufficient to inactivate the cellulase. In some aspects, the temperature is about 100° C.

U.S. Pat. No. 8,257,948 discloses some examples of purification steps that may be utilized in some embodiments of the methods disclosed herein to isolate or purify the glucosylated terpene glycoside.

PCT Publication No. WO 2017/089444 discloses some examples of purification steps that may be utilized in some embodiments of the methods disclosed herein to isolate or purify the glucosylated terpene glycoside.

PCT Publication No. WO 2013/019050 discloses some examples of purification steps that may be utilized in some embodiments of the methods disclosed herein to isolate or purify the glucosylated terpene glycoside.

European Patent Application Publication No. 3003058 discloses some examples of purification steps that may be utilized in some embodiments of the methods disclosed herein to isolate or purify the glucosylated terpene glycoside.

U.S. Pat. No. 8,257,948 discloses some examples of inactivation steps that may be utilized in some embodiments of the methods disclosed herein to isolate or purify the glucosylated terpene glycoside.

PCT Publication No. WO 2017/089444 discloses some examples of inactivation steps that may be utilized in some embodiments of the methods disclosed herein to isolate or purify the glucosylated terpene glycoside.

The Glucosylated Terpene Glycosides

In certain aspects, the disclosure provides a compound of formula I:

In certain aspects, the disclosure provides a compound of formula II:

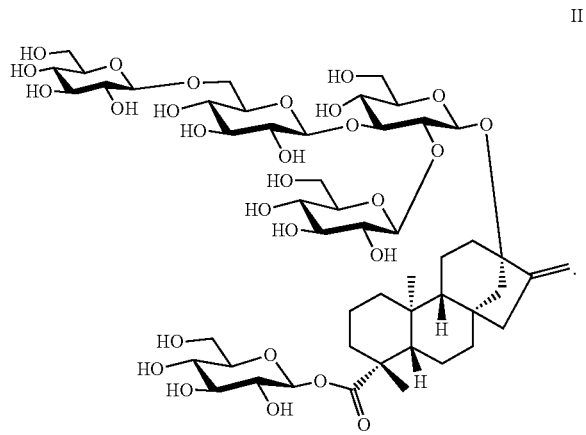

In certain aspects, the disclosure provides a compound of formula III:

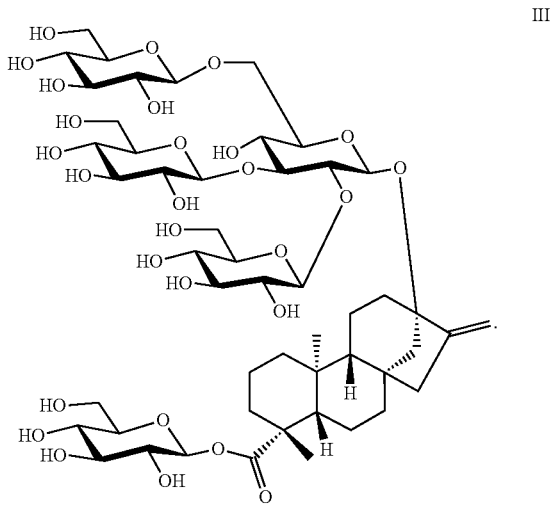

In certain aspects, the disclosure provides a compound of formula IV:

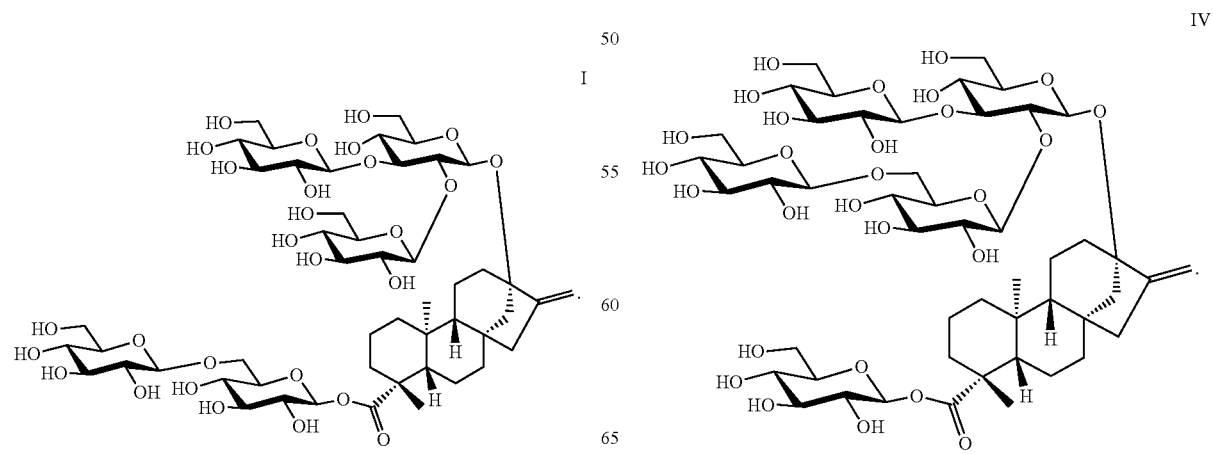

In some embodiments, the terpene glycoside is selected from the group consisting of: a compound of formula I, a compound of formula II and a compound of formula III, and a compound of formula IV.

As used herein, the foregoing compounds of formulas I to IV can also be referred to as "Compound I," "Compound II," "Compound III," and "Compound IV," respectively.

In some embodiments, the glucosylated terpene glycoside is mono β-1,6 glucosylated stevioside, mono β-1,6 glucosylated rebaudioside A, mono β-1,6 glucosylated rebaudioside B, mono β-1,6 glucosylated rebaudioside C, mono β-1,6 glucosylated rebaudioside D, mono β-1,6 glucosylated rebaudioside E, mono β-1,6 glucosylated rebaudioside F, mono β-1,6 glucosylated rebaudioside G, mono β-1,6 glucosylated rebaudioside M, mono β-1,6 glucosylated dulcoside A, mono β-1,6 glucosylated steviolbioside, mono β-1,6 glucosylated rubusoside, mono β-1,6 cellobiosylated stevioside, mono β-1,6 cellobiosylated rebaudioside A, mono β-1,6 cellobiosylated rebaudioside B, mono β-1,6 cellobiosylated rebaudioside C, mono β-1,6 cellobiosylated rebaudioside D, mono β-1,6 cellobiosylated rebaudioside E, mono β-1,6 cellobiosylated rebaudioside F, mono β-1,6 cellobiosylated rebaudioside G, mono β-1,6 cellobiosylated rebaudioside M, mono β-1,6 cellobiosylated dulcoside A, mono β-1,6 cellobiosylated steviolbioside, mono β-1,6 cellobiosylated rubusoside, or any mixture thereof.

Sweeteners or Sweetness Enhancers

The one glucosylated terpene glycoside described herein may be used as sweetness enhancers, flavor enhancers, taste maskers, or sweeteners in various flavored articles. In some embodiments, the glucosylated terpene glycoside is a glucosylated terpene glycoside having a single glucosyl residue linked to the terpene glycoside via a β-1,6 glucosidic bond. Alternatively, in some embodiments, the glucosylated terpene glycoside is a glucosylated terpene glycoside having a single cellobiosyl residue linked to the terpene glycoside via a β-1,6 glucosidic bond.

In certain aspects, the disclosure provides the use of at least one glucosylated terpene glycoside of the foregoing aspects and embodiments to confer, enhance, improve, or modify a sweet taste of a flavored article. In some embodiments, the glucosylated terpene glycoside is a glucosylated terpene glycoside having a single glucosyl residue linked to the terpene glycoside via a β-1,6 glucosidic bond. Alternatively, in some embodiments, the glucosylated terpene glycoside is a glucosylated terpene glycoside having a single cellobiosyl residue linked to the terpene glycoside via a β-1,6 glucosidic bond.

In certain aspects, the disclosure provides the use of at least one glucosylated terpene glycoside according to some aspects presented herein to mask a lingering taste of a flavored article. In some embodiments, the glucosylated terpene glycoside is a glucosylated terpene glycoside having a single glucosyl residue linked to the terpene glycoside via a β-1,6 glucosidic bond. Alternatively, in some embodiments, the glucosylated terpene glycoside is a glucosylated terpene glycoside having a single cellobiosyl residue linked to the terpene glycoside via a β-1,6 glucosidic bond.

In certain aspects, the disclosure provides a method, wherein the method confers, enhances, improves, or modifies a sweet taste of a flavored article, wherein the method comprises adding at least one glucosylated terpene glycoside having a single glucosyl residue linked to the terpene glycoside via a β-1,6 glucosidic bond according to some aspects presented herein to the flavored article, in an amount effective to confer, enhance, improve, or modify the sweet taste of the flavored article.

In certain aspects, the disclosure provides a method, wherein the method masks a lingering taste of a flavored article, wherein the method comprises adding the glucosylated terpene glycoside having a single glucosyl residue linked to the terpene glycoside via a β-1,6 glucosidic bond according to some aspects presented herein to the flavored article, in an amount effective to mask the lingering taste of a flavored article.

In certain aspects, the disclosure provides a method, wherein the method confers, enhances, improves, or modifies a sweet taste of a flavored article, wherein the method comprises adding at least one glucosylated terpene glycoside having a single cellobiosyl residue linked to the terpene glycoside via a β-1,6 glucosidic bond according to some aspects presented herein to the flavored article, in an amount effective to confer, enhance, improve, or modify the sweet taste of the flavored article.

In certain aspects, the disclosure provides a method, wherein the method masks a lingering taste of a flavored article, wherein the method comprises adding the glucosylated terpene glycoside having a single cellobiosyl residue linked to the terpene glycoside via a β-1,6 glucosidic bond according to some aspects presented herein to the flavored article, in an amount effective to mask the lingering taste of a flavored article.

In some embodiments, the amount effective to confer, enhance, improve, or modify the sweet taste of the flavored article is about 40 ppm, such as from 30 ppm to 50 ppm, or from 20 ppm to 60 ppm, or from 10 ppm to 70 ppm. In some embodiments, the amount effective to confer, enhance, improve, or modify the sweet taste of the flavored article is less than 40 ppm. In some aspects, the amount effective to confer, enhance, improve, or modify the sweet taste of the flavored article is greater than 40 ppm. In some embodiments, the amount effective to confer, enhance, improve, or modify the sweet taste of the flavored article is from 0 and 1000 ppm.

In some aspects, the disclosure provides flavored articles that comprise: the least one glucosylated terpene glycoside (of the foregoing aspects and embodiments); and a foodstuff base, wherein the glucosylated terpene glycoside is selected from the group consisting of: a glucosylated terpene glycoside having a single glucosyl residue linked to the terpene glycoside via a β-1,4 glucosidic bond, and a glucosylated terpene glycoside having a single cellobiosyl residue linked to the terpene glycoside via a β-1,4 glucosidic bond.

Suitable foodstuffs, e.g. foods or beverages are also provided herein. For the purpose of the present disclosure, "foodstuff base" means an edible product, e.g. a food or a beverage. Therefore, a flavored article provided herein comprises the functional formulation, as well as optionally additional benefit agents, corresponding to a desired edible product, e.g., a savory cube, and a flavor effective amount of the least one glucosylated terpene glycoside described herein. In some aspects, the glucosylated terpene glycoside is a glucosylated terpene glycoside having a single glucosyl residue linked to the terpene glycoside via a β-1,6 glucosidic bond. Alternatively, in some aspects, the glucosylated terpene glycoside is a glucosylated terpene glycoside having a single cellobiosyl residue linked to the terpene glycoside via a β-1,6 glucosidic bond.

The compositions and methods provided herein have use in food or beverage products. When the food product is a particulate or powdery food, the dry particles may easily be added thereto by dry-mixing. Typical food products are selected from the group consisting of an instant soup or sauce, a breakfast cereal, a powdered milk, a baby food, a powdered drink, a powdered chocolate drink, a spread, a powdered cereal drink, a chewing gum, an effervescent tablet, a cereal bar, and a chocolate bar. The powdered foods or drinks may be intended to be consumed after reconstitution of the product with water, milk and/or a juice, or another aqueous liquid.

The food product may be selected from the group consisting of condiments, baked goods, powdery food, bakery filings and fluid dairy products.

Condiments include, without limitation, ketchup, mayonnaise, salad dressing, Worcestershire sauce, fruit-flavored sauce, chocolate sauce, tomato sauce, chili sauce, and mustard.

Baked goods include, without limitation, cakes, cookies, pastries, breads, donuts and the like.

Bakery fillings include, without limitation, low or neutral pH fillings, high, medium or low solids fillings, fruit or milk based (pudding type or mousse type) fillings, hot or cold make-up fillings and nonfat to full-fat fillings.

Fluid dairy products include, without limitation, non-frozen, partially frozen and frozen fluid dairy products such as, for example, milks, ice creams, sorbets and yogurts. Beverage products include, without limitation, carbonated soft drinks, including cola, lemon-lime, root beer, heavy citrus ("dew type"), fruit flavored and cream sodas; powdered soft drinks, as well as liquid concentrates such as fountain syrups and cordials; coffee and coffee-based drinks, coffee substitutes and cereal-based beverages; teas, including dry mix products as well as ready-to-drink teas (herbal and tealeaf based); fruit and vegetable juices and juice flavored beverages as well as juice drinks, nectars, concentrates, punches and "ades"; sweetened and flavored waters, both carbonated and still; sport/energy/health drinks; alcoholic beverages plus alcohol-free and other low-alcohol products including beer and malt beverages, cider, and wines (still, sparkling, fortified wines and wine coolers); other beverages processed with heating (infusions, pasteurization, ultra-high temperature, ohmic heating or commercial aseptic sterilization) and hot-filled packaging; and cold-filled products made through filtration or other preservation techniques.

The nature and type of the constituents of the foodstuffs or beverages do not warrant a more detailed description here, which in any case would not be exhaustive, the skilled person being able to select them on the basis of his general knowledge and according to the nature of the product.

The proportions in which the least one glucosylated terpene glycoside described herein can be incorporated into the various aforementioned articles or compositions vary within a wide range of values. These values are dependent on the nature of the article to be flavored and on the desired organoleptic effect as well as the nature of the co-ingredients in a given base when the compounds according to the invention are mixed with flavoring co-ingredients, solvents or additives commonly used in the art.

In the case of flavoring compositions, typical concentrations are in the order of about 0.0001 wt % to 1 wt %, or even more, of the least one glucosylated terpene glycoside described herein based on the weight of the consumer product into which they are incorporated. Concentrations lower than these, such as in the order of 0.001 wt % to 0.5 wt % by weight, can be used when the least one glucosylated terpene glycoside described herein are incorporated into flavored articles, percentage being relative to the weight of the article.

EXAMPLES

Example 1: Generation of Mono β-1,6-glucosylated Terpene Glycoside Compounds (Compounds I and II) Using Rebaudioside A as a Starting Material by a Method According to Some Aspects Presented Herein Rebaudioside A (0.5 g) and cellobiose (0.5 g) were dissolved in 12 ml NaOAc-HOAc (pH=5.0, 0.2 M) buffer at room temperature. Subsequently, 0.5 g methaplus L110 (DSM) was added to the mixture. The mixture containing the enzyme was then heated to 37° C., and the mixture containing the enzyme was incubated at 37° C. for 24 hours to allow the transglucosidation reaction to proceed, thereby generating the at least one glucosylated terpene glycoside having a single glucosyl residue linked to the terpene glycoside via a β-1,6 glucosidic bond. The reaction was terminated by inactivating the cellulase by incubating the reaction mixture at 100° C. for 30 minutes.

The resulting reaction mixture was analyzed by UPLC-UV, and a mixture containing glucosylated terpene glycosides having a single glucosyl residue linked to the terpene glycoside via a β-1,6 glucosidic bond was identified (see FIG. 1). The identified mixture was purified via a prep-LC. The compounds within the mixture were identified as compounds I and II, at a concentration of 3.7% and 4.0% in the mixture, respectively.

In a separate experiment, rebaudioside A (0.5 g) and cellobiose (0.5 g) were dissolved in 12 ml NaOAc-HOAc (pH=5.0, 0.2 M) buffer at room temperature. Subsequently, 0.5 g cellulase (Aladdin) was added to the mixture. The mixture containing the enzyme was then heated to 37° C., and the mixture containing the enzyme was incubated at 37° C. for 24 hours to allow the transglucosidation reaction to proceed, thereby generating the at least one glucosylated terpene glycoside having a single glucosyl residue linked to the terpene glycoside via a β-1,6 glucosidic bond. The reaction was terminated by inactivating the cellulase by incubating the reaction mixture at 100° C. for 30 minutes.

Figure 2:
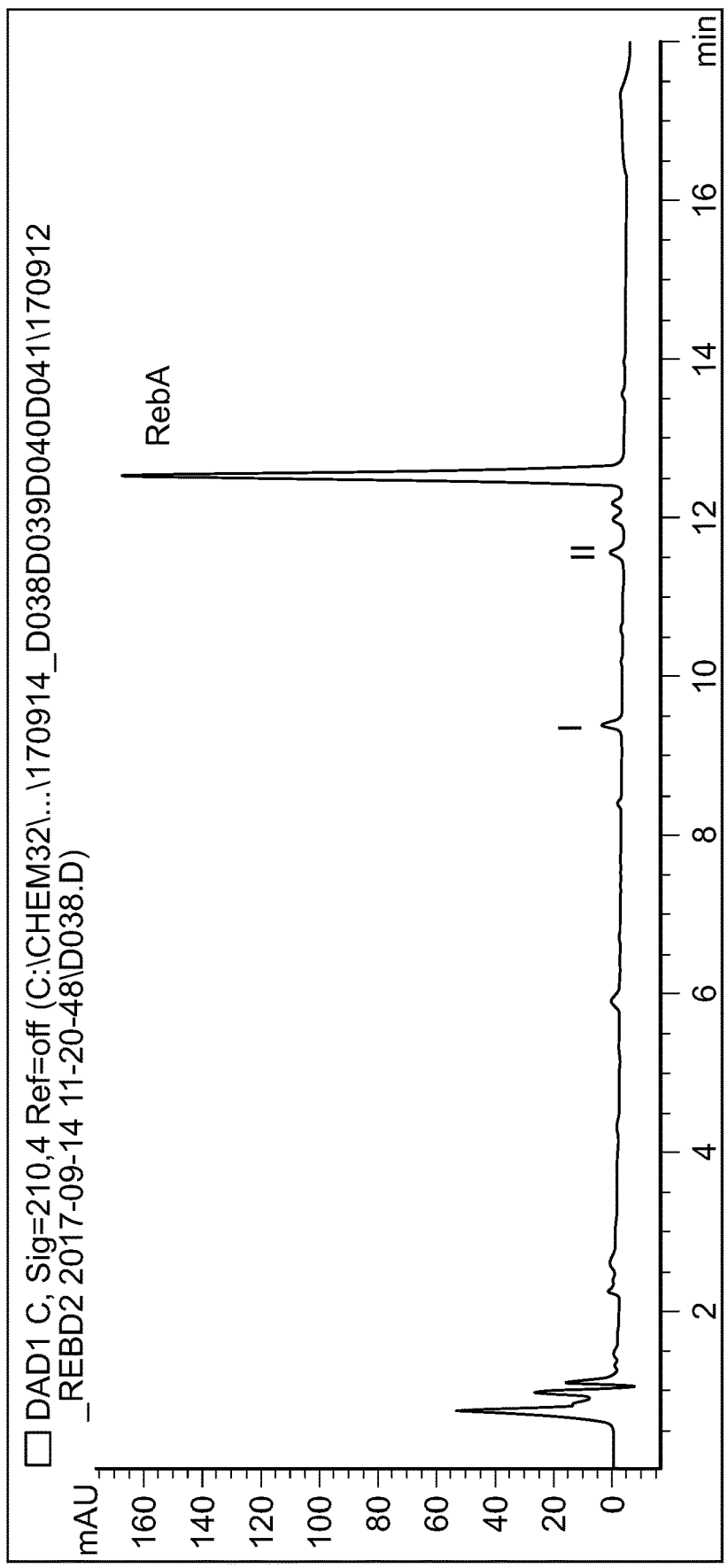
FIG. 2 show an HPLC chromatogram of the product enzymatically generated by cellulase with rebaudioside A and cellobiose as substrates.

The resulting reaction mixture was analyzed by UPLC-UV, and a mixture containing glucosylated terpene glycosides having a single glucosyl residue linked to the terpene glycoside via a β-1,6 glucosidic bond was identified (see FIG. 2). The identified mixture was purified via a prep-LC. The compounds within the mixture were identified as Compounds I and II, at a concentration of 3.2% and 2.6% in the mixture, respectively.

In a separate experiment, rebaudioside A (0.5 g) and cellobiose (0.5 g) were dissolved in 12 ml NaOAc-HOAc (pH=5.0, 0.2 M) buffer at room temperature. Subsequently, 0.5 g Cellucast (Novozymes) was added to the mixture. The mixture containing the enzyme was then heated to 37° C., and the mixture containing the enzyme was incubated at 37° C. for 24 hours to allow the transglucosidation reaction to proceed, thereby generating the at least one glucosylated terpene glycoside having a single glucosyl residue linked to the terpene glycoside via a β-1,6 glucosidic bond. The reaction was terminated by inactivating the cellulase by incubating the reaction mixture at 100° C. for 30 minutes.

Figure 3:
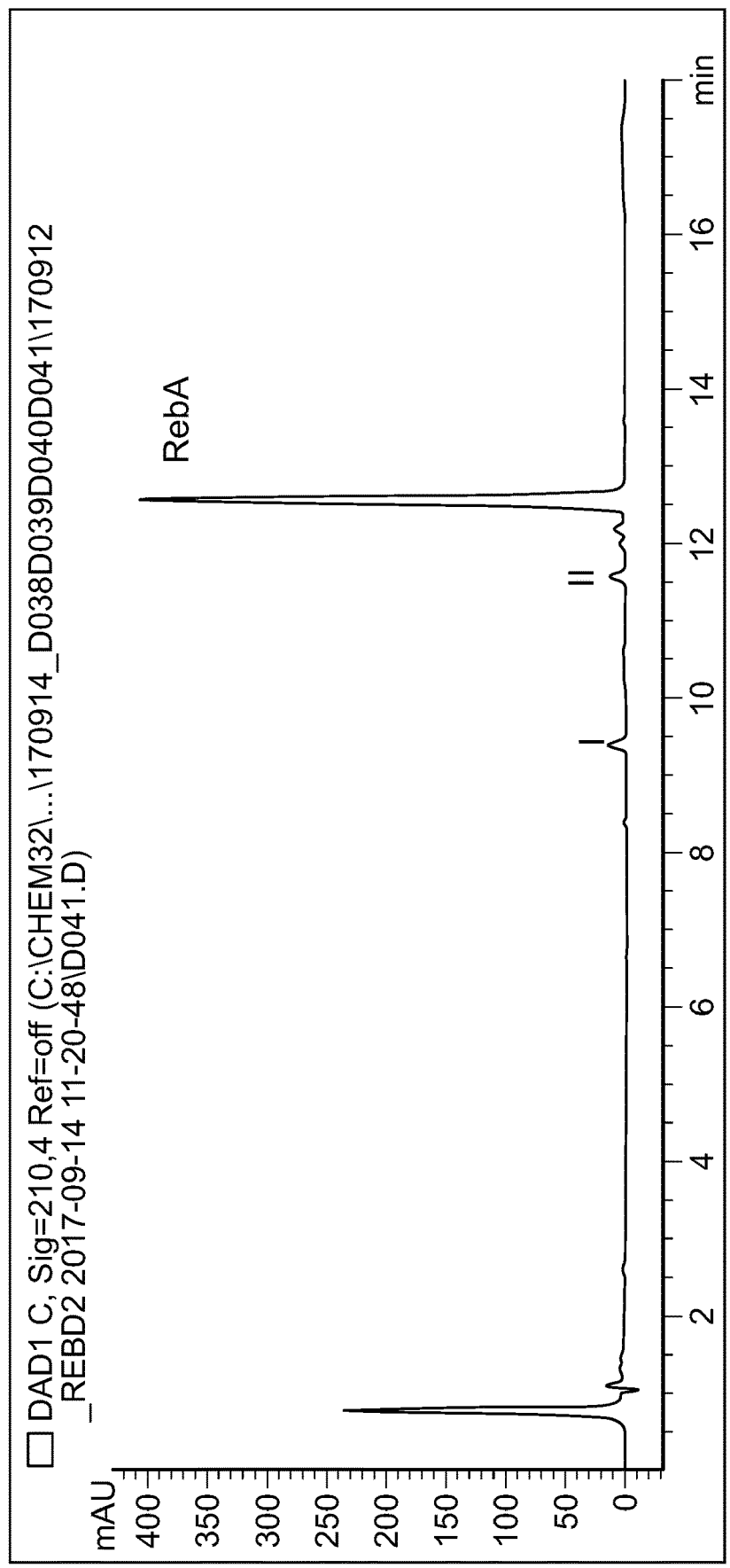
FIG. 3 shows an HPLC chromatogram of the product enzymatically generated by cellulase with rebaudioside A and cellobiose as substrates.

The resulting reaction mixture was analyzed by UPLC-UV, and a mixture containing glucosylated terpene glycosides having a single glucosyl residue linked to the terpene glycoside via a β-1,6 glucosidic bond was identified (see FIG. 3). The identified mixture was purified via a prep-LC. The compounds within the mixture were identified as compounds of formulas I and II, at a concentration of 3.2% and 2.6% in the mixture, respectively.

Figure 4:
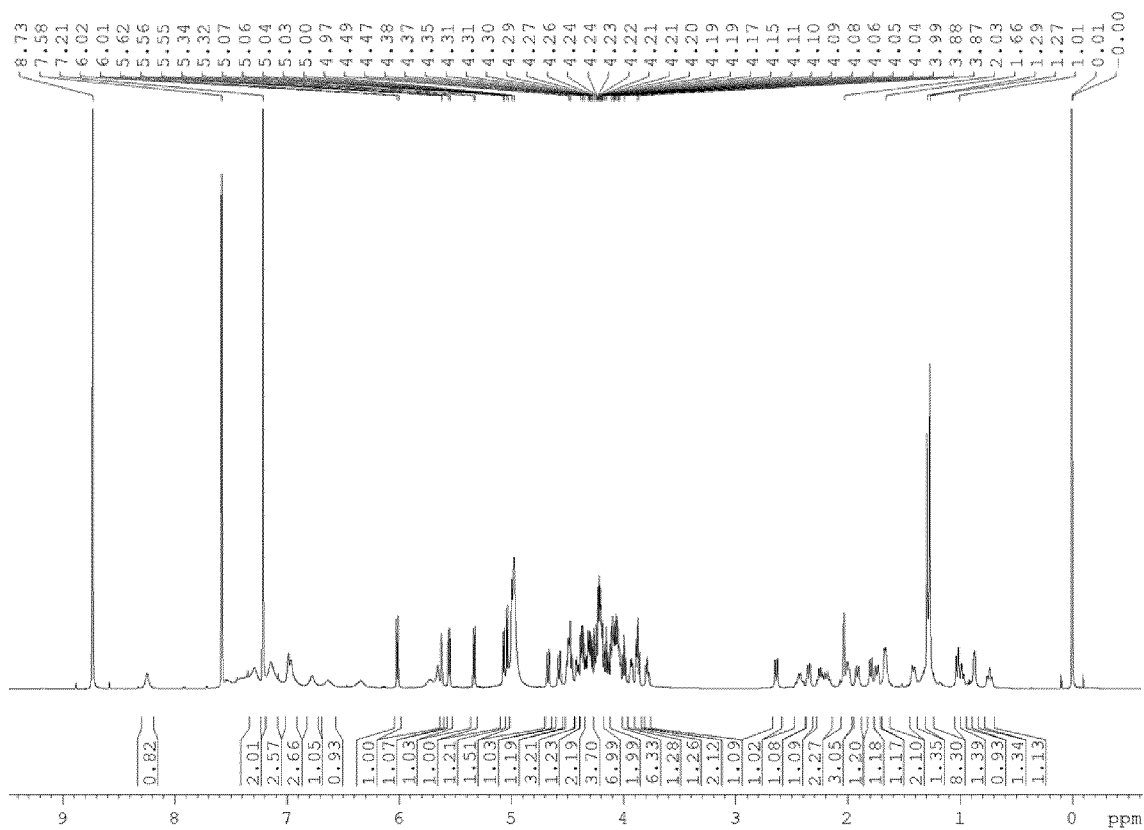
FIG. 4 shows A $^1$H NMR spectrum for a composition comprising the compound of formula I.
Figure 5:
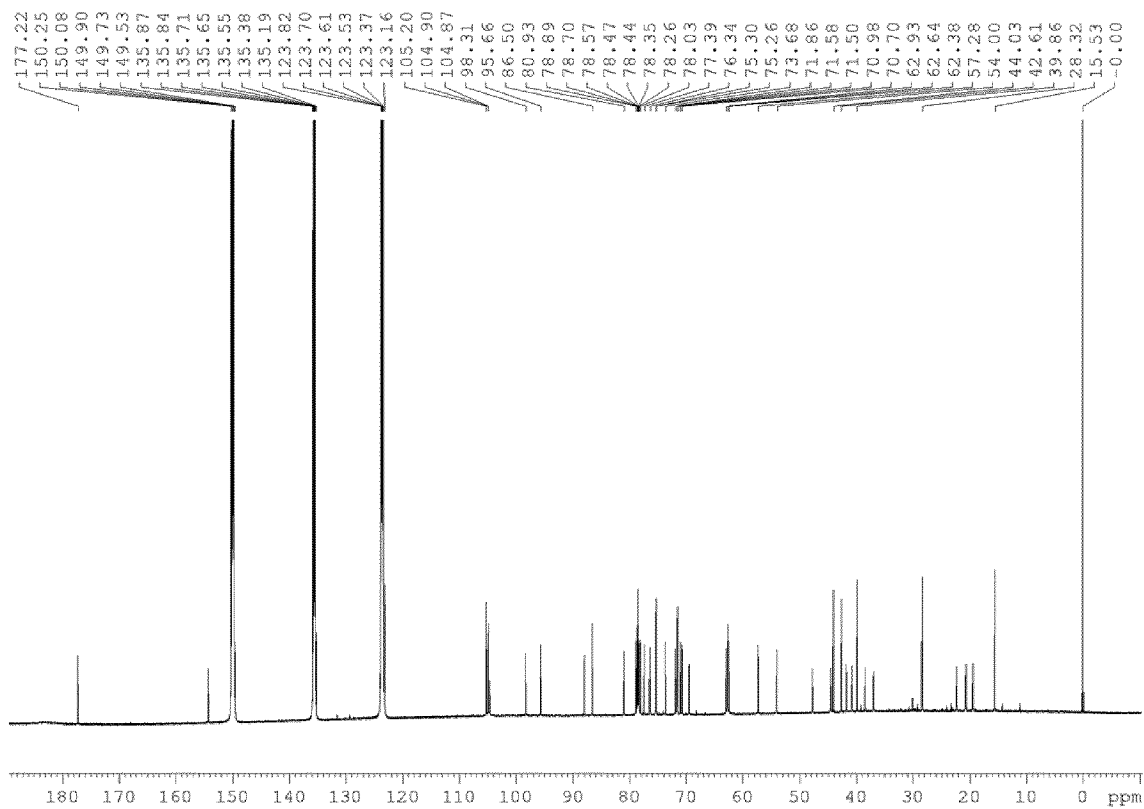
FIG. 5 shows A $^{13}$C NMR spectrum for a composition comprising the compound of formula I.
Figure 6:
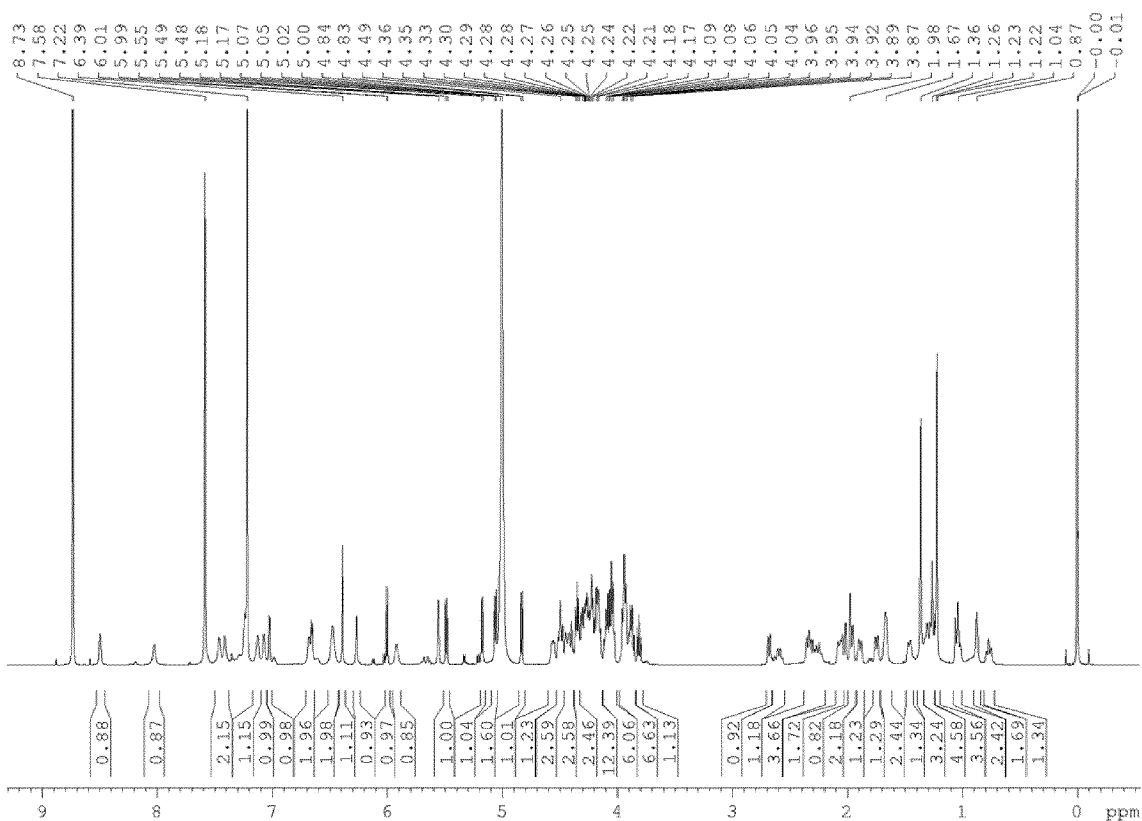
FIG. 6 shows A $^1$H NMR spectrum for a composition comprising the compound of formula II.
Figure 7:
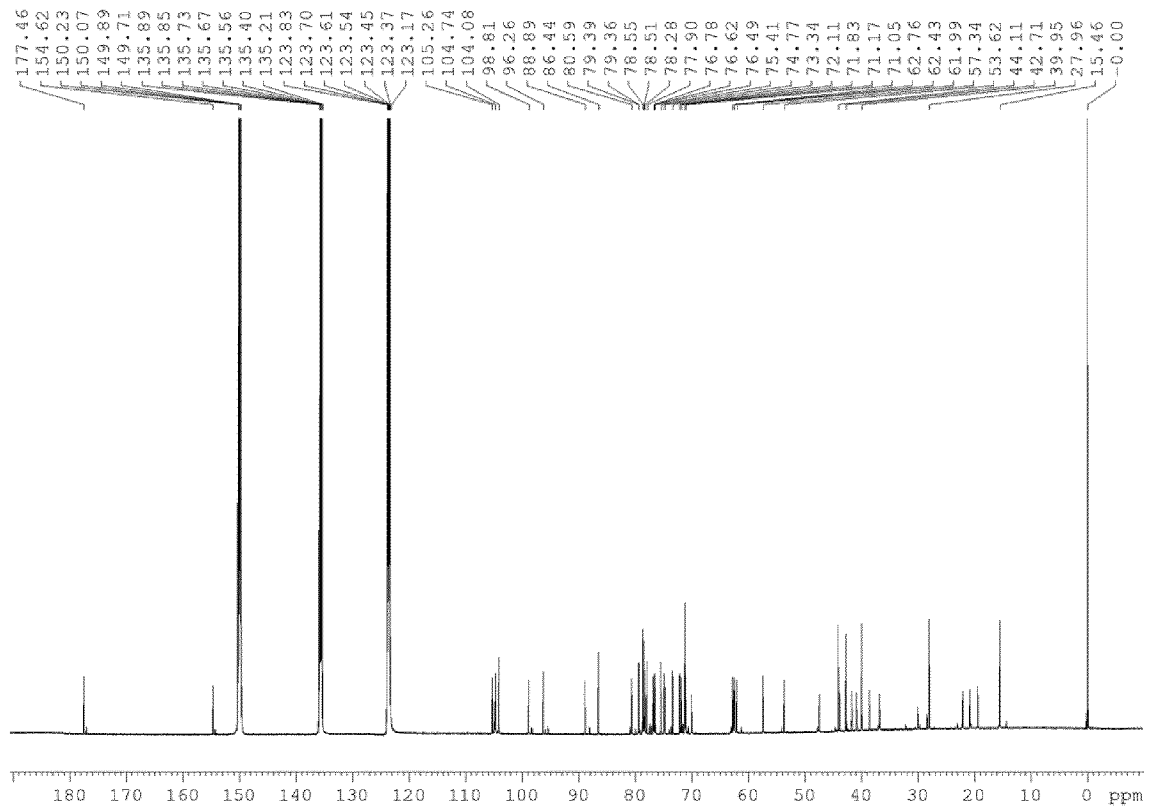
FIG. 7 shows A $^{13}$C NMR spectrum for a composition comprising the compound of formula II.

FIG. 4 shows A $^1$H NMR spectrum for a composition comprising the compound of formula I FIG. 5 shows A $^{13}$C NMR spectrum for a composition comprising the compound of formula I. FIG. 6 shows A $^1$H NMR spectrum for a composition comprising the compound of formula II FIG. 7 shows A $^{13}$C NMR spectrum for a composition comprising the compound of formula II.

Example 2: Sensory Properties of a Composition Comprising Compounds I and II

A composition comprising Compound I was generated according to the methods described in Example 1. The composition was dissolved in a 4% w/w sucrose solution, at a final concentration of 30 ppm. A panel of 8 trained people evaluated the test solution, as well as samples comprising rebaudioside A, rebaudioside D, or rebaudioside M for taste properties (sweet, licorice and sweet lingering). The results are shown in the table below.

| Product | Description |
| --- | --- |
| Sucrose | Sweet, slightly lingering |
| Compound I | Sweet, licorice, lingering |
| Reb A | Sweet, licorice, lingering, slightly astringent |
| Reb D | Sweet, lingering, licorice |
| Reb M | Licorice, sweet, lingering |

All samples were sweet at 30 ppm, where sucrose has weaker lingering taste than others. Rebaudioside M was found to have a stronger licorice taste, compared to the other samples. These data suggest that the compound of formula I may be used as a sweetener.

In another experiment, a composition comprising compound of formula I was generated according to the methods described in Example 1. The composition was dissolved in a 4% w/w sucrose solution. A panel of 8 trained people evaluated the test solutions for taste properties (sweet, licorice and sweet lingering) on a scale of −5 to 5 (−5 denoted no effect and 5 denoted extremely strong effect, 0 being the intensity of a reference water solution containing either (i) 4% w/w sucrose solution. The results are shown in the table below.

| Product | Sweet | Licorice | Sweet Lingering |
| --- | --- | --- | --- |
| Compound I | 1.1 | 1.4 | 0.4 |
| Significant level | * | | |
| Reb A | 1.5 | 1.3 | 0.5 |
| Significant level | ** | | * |
| Reb D | 1.5 | 1.3 | 0.4 |
| Significant level | ** | | |
| Reb M | 1.6 | 1.3 | 0.8 |
| Significant level | *** | ** | ** |

At a dosage of 30 ppm, Compound I significantly enhanced the sweet intensity in the 4% sucrose base (at 95% of confidence level) without any significant effect for licorice and sweet lingering tastes.

When compared to other samples, such as rebaudioside A, rebaudioside D and rebaudioside M, Compound I had a similar effect as rebaudioside D, yet was better than rebaudioside A (enhancing sweet and sweet lingering tastes) and rebaudioside M (enhancing all sweet, licorice and sweet lingering tastes).

The invention claimed is:

1. A compound, which is (a) a compound of formula I, a compound of formula II, a compound of formula III, or a compound of formula IV:

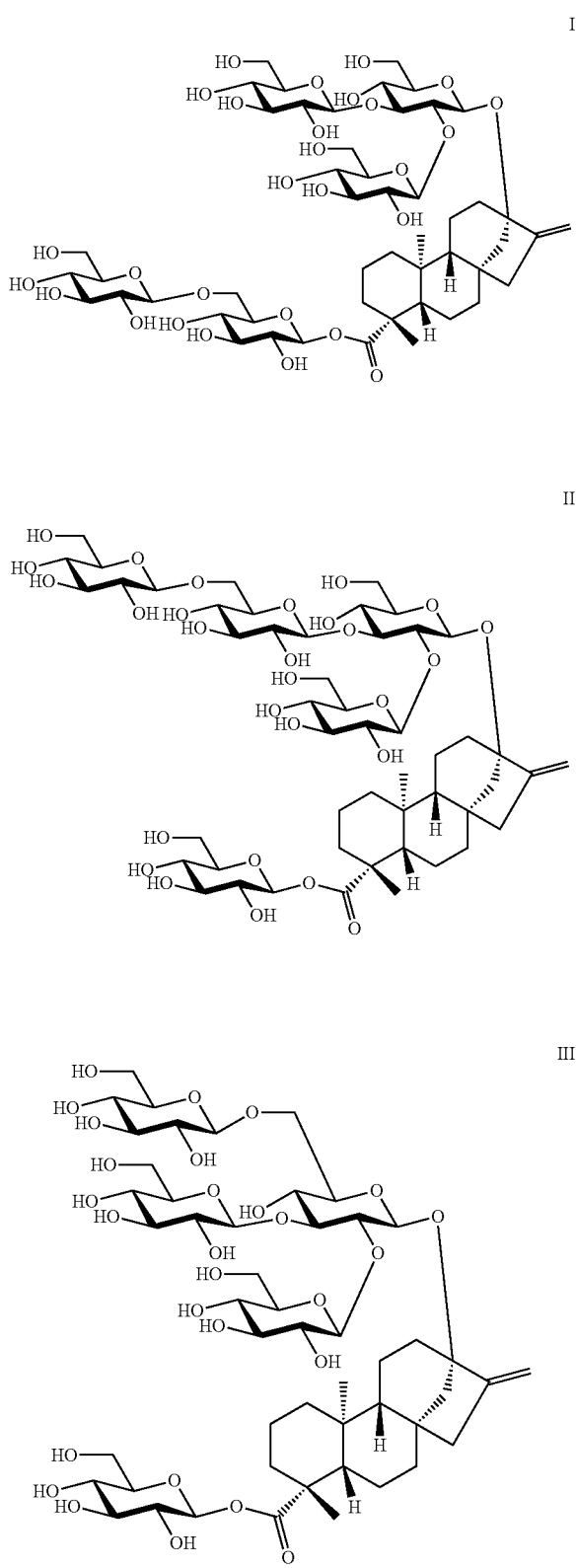

-continued
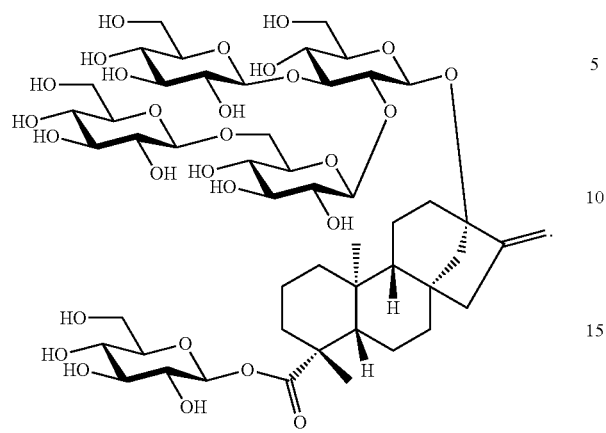
IV
2. A flavored article, which comprises a carrier and the glucosylated terpene glycoside of claim 1.
* * * * *